United States Patent
Birnbaum

(10) Patent No.: US 6,441,045 B1
(45) Date of Patent: Aug. 27, 2002

(54) DISINFECTANT COMPOSITION

(76) Inventor: Bernardo Birnbaum, Hospital de Clinicas Caracas Calle Alameda con Av., Panteon, Piso 4, oficina 420, San Bernandino Caracas (VE)

( * ) Notice: Subject to any disclaimer, the term of this patent is extended or adjusted under 35 U.S.C. 154(b) by 0 days.

(21) Appl. No.: 09/433,537

(22) Filed: Nov. 3, 1999

Related U.S. Application Data

(63) Continuation-in-part of application No. 08/986,365, filed on Dec. 8, 1997, now abandoned.

(51) Int. Cl.$^7$ .................. A01N 33/12; A01N 25/00; A01N 37/00; A01N 59/02

(52) U.S. Cl. .................. 514/643; 424/710; 424/713; 424/719; 514/574; 514/769; 514/784; 514/970; 514/974

(58) Field of Search .................. 424/405, 710, 424/713, 719, 770; 422/28, 37; 514/642, 643, 647, 740, 741, 743, 751, 574, 769, 784, 970, 974

(56) References Cited

U.S. PATENT DOCUMENTS

| | | | | |
|---|---|---|---|---|
| 3,629,330 A | * | 12/1971 | Brody et al. | 260/553 |
| 3,810,478 A | * | 5/1974 | Olson, Jr. et al. | 132/7 |
| 4,224,319 A | * | 9/1980 | Marcadet | 424/238 |
| 4,548,716 A | * | 10/1985 | Boeve | 210/652 |
| 5,094,743 A | * | 3/1992 | Miller et al. | 424/78.04 |

FOREIGN PATENT DOCUMENTS

GB 1357731 A * 6/1974

OTHER PUBLICATIONS

Remington's Pharmaceutical Sciences (17th Ed. 1985), pp. 243–244, 369–370, 1293, 1494, 1495, 1520, 1522.*

Hutcheson, 'Alternatives to distillation in the production of WFI quality water', Elsevier Science Ltd. (1995), pp. 941–945.*

Osmonics, Inc., 'Methods of water purification', National Development (1992), excerpted from "Pure Water Handbook", pp. 2–6.*

Weitnauer, 'Pharmaceutical: A practical approach to controllin g microbial growth in USP', Ultrapure Water (1996), pp. 2–4.*

* cited by examiner

*Primary Examiner*—Jose' G. Dees
*Assistant Examiner*—Frank Choi
(74) *Attorney, Agent, or Firm*—Hughes Hubbard & Reed LLP; Ronald Abramson; Sheryl L. Sandridge

(57) ABSTRACT

A disinfectant composition containing more than 0.05% and less than 9.4% by volume of dimethyl benzyl lauryl ammonium bromide, substantially pure, substantially de-ionized, substantially bacteria free water if the pH of the water is between 5.0 and 6.8, a first stabilizer structured to adjust a pH level of the disinfectant composition to approximately 7, ammonium Bulfate structured to increase a strength of the composition and a stabilizer structured to lower the pH level of the disinfectant composition back to approximately 7.

4 Claims, No Drawings

DISINFECTANT COMPOSITION

This is a continuation-in-part which claims the priority of my application, Ser. No. 08/986,365, filed Dec. 8, 1997, now abandoned.

BACKGROUND OF THE INVENTION

1. Field of the Invention

The present invention relates to a disinfectant composition which can be safely and effectively utilized as a disinfectant, bactericide, fungicide, cold sterilizer, virucide and the like, and which in addition to being highly effective for the eradication of germs, viruses, fungus and bacteria in a variety of uses, is odorless, colorless, non-toxic, non-corrosive, non-flammable, and non-staining.

2. Description of the Related Art

Many different types of disinfectants, bactericides, fungicides, cold sterilizers and the like have been in use in a variety of industries, including the pharmaceutical and medical industries, for some time. Typically, these chemicals have been utilized as replacements to heat sterilization, radiation sterilization, or other less desirable techniques, in order to effectuate a more cost effective, convenient and/or presumably safer manner of eliminating potentially harmful germs, viruses, funguses and bacteria. Additionally, however, a prominent consideration has always been the strength or power of the chemical disinfectant as compared with other methods. Indeed, it is the general desirability for a more effective or powerful product which has, in some industries, resulted in effectiveness and cost outweighing safety. For this reason, very stringent guidelines are placed on all chemical disinfectant compositions and a user must take great care on the nature of the use to which a chemical disinfectant is being put.

As can be appreciated, a variety of different chemical composition and solutions have been provided in various industries, each solution claiming to have different and/or better qualities than other chemicals also available for the same purposes. Moreover, while each chemical does have certain beneficial attributes, typically, particular chemicals are tailored for particular industries based upon the nature and/or tolerances of the articles to be disinfected. For example, chemicals utilized for disinfecting floors and walls tend to be stronger and harsher than chemicals utilized for disinfecting surgical equipment, human or animal patients or even food products. As such, the present art lacks an effective chemical composition which is substantially effective for a multitude of cross over uses and in any of a variety of different industries wherein such disinfection or sterilization is needed, with little or no modification.

Despite the specialization of particular chemicals, a primary drawback associated with substantially all effective disinfectant or sterilization chemical formulations, and indeed a primary reason for lack of multi-purpose use ability, is the corrosive and/or toxic nature of the chemical compositions. For example, even though such concerns are not as significant when dealing with an industrial setting wherein machinery or floors must be cleaned or sterilized, the health of the workers that are charged with the disinfecting and sterilizing duty, as well as of the workers who must be present in a vicinity of the area that has just been cleaned, nevertheless make the toxic and corrosive nature of industrial cleaners a concern. Of course, in other industries wherein the articles to be cleaned are more sensitive or come into closer contact with a human, such as for the sterilization of surgical equipment and food products, any toxic or corrosive qualities exhibited by the chemical will render that chemical not useable for the particular tasks. Accordingly, even the presently available chemicals which are being marketed and utilized are either generally ineffective or are overly corrosive for complete safety. It is for those very reasons that other methods of cleaning and/or sterilization are constantly being sought. As such, there is a substantial need in the art for a non-toxic and non-corrosive chemical disinfectant/sterilizer which is highly effective and eliminates substantially all harmful germs, funguses, viruses and bacteria present in a treated article. Moreover, it would be highly beneficial to provide such a chemical composition which can be used topically on living human or animal patients without any harmful results to the patient, and can be utilized even on the most sensitive of articles, such as medical equipment including plastics, metals, glass, rubber, optics structures and the like.

It is also noted, that of the various disinfectant and sterilization chemicals presently available, a number of them implement a quaternary ammonium salt as a primary active ingredient in the chemical formulation. Such existing formulations, however, while seeking to benefit from the potential of the quaternary ammonium salt for eliminating germs, viruses, funguses and bacteria, have not been capable of providing a truly effective and safe chemical formulation that utilizes the beneficial aspects of the quaternary ammonium salt, but which also avoids the highly toxic and corrosive aspects thereof. Indeed, those in the art have sought to implement a wide variety of different formulations and chemical additives, however, the finished chemical products have proven to either be generally ineffective or remain substantially corrosive and toxic. For example, previously known or utilized diluents have generally rendered the product ineffective or have not eliminated its corrosivity or toxicity. Therefore such known quaternary ammonium salt based disinfectants and sterilizers have generally been limited to isolated industrial type uses.

As a result, it would be highly beneficial to provide an improved disinfectant and cold sterilizer which can utilize the bacteria, virus, fungus and germ killing effects of a quaternary ammonium salt, but which recognizes the specific benefits of utilizing a particular quaternary ammonium salt in a particular chemical formulation in order to achieve substantially unexpected and remarkably safe bacteria, virus, fungus and germ killing results in a safe, yet effective manner. Moreover, such a product, in addition to being safe, non-toxic, and non-corrosive should not compromise effectiveness in favor of that safety, non-corrosivity and non-toxicity. The disinfecting composition of the present invention achieves such a solution.

SUMMARY OF THE INVENTION

The present invention is directed towards a disinfectant composition to be utilized to disinfect or sterilize a variety of articles including surfaces, medical instruments and equipment, living human and animal patients, foods, plants, and contaminated fluid bodies.

Specifically, the present invention includes a disinfectant composition containing between 0.05% and 9% by volume of Dimethyl Benzyl Lauryl Ammonium Bromide as part of an initial base mixture. Moreover, the disinfectant composition further includes water which is substantially pure, substantially bacteria free and substantially ion free. Furthermore, the water has preferably been treated so as to be sufficiently pure, ion-free and bacteria free such that a relatively large volume of water is utilized to act as a diluent of the Dimethyl Benzyl Lauryl Ammonium Bromide and create a stable, safe and effective base mixture, without minerals or other impurities usually present in water adversely reacting with the Dimethyl Benzyl Lauryl Ammonium Bromide and reducing the effectiveness thereof and/or causing harmful characteristics to be exhibited thereby.

The pH of the pure water available for use in connection with the invention varies from one place to another. Therefore, depending on the pH of the water, there are two formulas, which provide alternate embodiments of the invention.

A first preferred disinfectant composition of the present invention is used when the pH of the water used in the composition is between about 7.0 and 8.8. Dimethyl benzyl lauryl ammonium bromide is added in the amount of 0.05 to 9.4 g. per 100 ml. of solution, and preferably 0.17 g. per 100 ml. of solution, increasing the pH to about 8.8 to 9.2. A strengthening additive, ammonium sulfate, is added, preferably in a solution of approximately 50 g. per 100 ml. of water (preferably the substantially pure, substantially de-ionized, substantially bacteria free water otherwise used in this invention), until the pH decreases to about 7.7 to 7.8. If desired, citric acid may then be added as a stabilizer to further reduce the pH to between about 6.8 and 7.2 (although additional ammonium sulfate solution may be added to achieve substantially the same pH adjustment).

A second preferred disinfectant composition of the present invention further includes a first, a second, and a third additive included therewith. The first additive is base structured to be added to the mixture of Dimethyl Benzyl Lauryl Ammonium Bromide and substantially pure, substantially de-ionized, substantially bacteria free water in order to adjust a pH level of the base mixture to between about 6.8 and 7.2.

The second additive, which is preferably ammonium sulfate in a quantity of less than 2% by volume, further defines a strengthening additive and is structured to be added to the base mixture, after the first stabilizer has been added to the base mixture and has adjusted the pH level thereof. The second additive is structured to increase a strength and effectiveness of Dimethyl Benzyl Lauryl Ammonium Bromide. As used herein, unless otherwise specified, "by volume" with reference to solid additives and stabilizers means weight-volume (w-v) percent, that is, grams solute per 100 ml. of solution.

The third additive, which is preferably added after the first and second additives have been added and have taken effect, is structured to lower the pH level of the disinfectant composition back to between about 6.8 and 7.2. This provides a stabilized disinfecting composition having a pH level of between 6.8 and 7.2 which can be utilized directly for a variety of uses, such as pharmaceutical uses. Moreover, the base mixture, either with or without the stabilizers, can be combined with various other ingredients or carriers, such as color, fragrance, or viscosity adjusting compounds, without perturbance of the safety and effectiveness of the disinfectant composition in its final application.

It is also seen that the present invention is directed towards a method manufacturing a disinfecting composition. Specifically, the method of the preferred embodiment includes an initial step of purifying a quantity of water to at least a 98% purity level. Additionally, the water, either before or after, but preferably during, purification, is also de-ionized to be at least 98% ion free. Once the quantity of at least 98% pure, at least 98% de-ionized, and at least 98% bacteria free water is attained, it is mixed with a quantity of Dimethyl Benzyl Lauryl Ammonium Bromide to define a base mixture. Preferably, between 0.05% and 9% by volume of the Dimethyl Benzyl Lauryl Ammonium Bromide is provided in the base mixture, with the water preferably comprising the remaining amounts of the base mixture and thereby substantially diluting the Dimethyl Benzyl Lauryl Ammonium Bromide.

Next, a pH level of the base mixture is preferably measured and adjusted to a pH level of between approximately 6.8 and 7.2. Moreover, in a preferred embodiment, this adjustment phase can include a series of distinct steps to arrive at that final pH level of between approximately 6.8 and 7.2. In particular, a first stabilizer is preferably added in sufficient quantity to the base mixture of Dimethyl Benzyl Lauryl Ammonium Bromide and substantially pure, substantially de-ionized, substantially bacteria free water in order to bring the pH level to between 6.8 ad 7.2. Subsequently, however, a second additive, preferably ammonium sulfate, is added to the base mixture. This second additive is preferably a strengthening additive structured to boost a strength and effectiveness of the Dimethyl Benzyl Lauryl Ammonium Bromide contained within the base mixture. Lastly, and especially in a pharmaceutical application, the pH level of the composition is preferably further adjusted by adding a stabilizer, back to a pH level between 6.8 and 7.2 so as to produce the effective disinfectant composition. Indeed, the disinfectant composition produced is structured such that it can be combined with other additives and carriers, such as coloring agents, fragrance additives, cleaning agents and the like, without losing its effectiveness for eliminating germs, viruses, funguses and bacteria, and without becoming toxic or corrosive, presuming of course that the further compositions added are not toxic or corrosive in and of themselves and do not adversely react with the Dimethyl Benzyl Lauryl Ammonium Bromide.

It is an object of the present invention to produce a disinfecting composition which utilizes the beneficial effects of Dimethyl Benzyl Lauryl Ammonium Bromide in a highly effective, yet safe, non-toxic, non-corrosive, non-flammable, non-staining, colorless and odorless fashion.

A further object of the present invention is to produce a highly effective disinfectant composition which can be utilized as a cold sterilizer for a variety of articles such as surgical and clinical equipment (for example: scopes, rods, lenses, tubes, etc.), and which in addition to being highly effective is substantially non-corrosive or non-toxic.

Yet another object of the present invention is to provide a disinfecting composition which can be effectively utilized topically on living patients, such as animal or human patients, in order to disinfect a wound or other contaminated area.

Also an object of the present invention is to provide a disinfecting composition which can be effectively utilized to kill germs and bacteria on foods and plants prior to their being made available for public consumption, and which is substantially safe and non-toxic in addition to being highly effective.

A further object of the present invention is to provide a disinfecting composition which is capable of boosting the effects of Dimethyl Benzyl Lauryl Ammonium Bromide contained in a safe, non-toxic, non-corrosive composition.

Another object of the present invention is to provide a disinfecting composition which utilizes Dimethyl Benzyl Lauryl Ammonium Bromide safety and effective, and which eliminates the reactivity of Dimethyl Benzyl Lauryl Ammonium Bromide with minerals and ions typically contained in a diluent such as water, thereby maintaining the effectiveness of the disinfectant composition despite its being substantially diluted into a non-toxic and non-corrosive composition.

Yet another object of the present invention is to provide a disinfecting composition which can be effectively utilized as a safe fungicide for human, veterinary and other applications.

Another object of the present invention is to provide a disinfecting composition which can be effectively utilized to eliminate oil contaminants in a variety of applications, such as increasing the purity and effectiveness of fuel, cleaning pumps, drills and pipe lines, countering the toxic and harmful effects of oil spills, and the like.

An added object of the present invention is to provide a disinfecting composition which can be effectively utilized as a safe food preservative, contact lens cleaning solution, a safe cleaner, such as for art work, and an air or air conditioning system disinfectant.

DETAILED DESCRIPTION OF THE PREFERRED EMBODIMENT

The present invention is directed towards a disinfecting composition having a variety of multi-industrial, clinical and ecological uses which involve the elimination of germs, fungus, viruses and bacteria in a non-toxic, colorless, non-corrosive, nonflammable, non-staining, and odorless manner. The disinfecting composition of the present invention includes primarily a quantity of a quaternary ammonium salt, which is ideally Dimethyl Benzyl Lauryl Ammonium Bromide. In particular, Dimethyl Benzyl Lauryl Ammonium Bromide is seen to have highly beneficial germ, fungus, virus and bacteria eliminating properties and is substantially effective with the composition of the present invention in order to achieve a substantially safe, yet effective product. The Dimethyl Benzyl Lauryl Ammonium Bromide included in the disinfecting composition of the present invention is provided in a quantity of less than 9.4% by volume. In the preferred embodiment, however, between 0.05% and 9% by volume of Dimethyl Benzyl Lauryl Ammonium Bromide is included, with the actual percentage depending upon the ultimate application of the disinfectant composition. By way of illustration, a 9% by volume concentration can be used for cleaning floors and walls, and a preferred 0.2% by volume concentration is used for human topical applications. Furthermore, it is preferred that the Dimethyl Benzyl Lauryl Ammonium Bromide be at least 91%, pure, and in the preferred embodiment a purity level of 95% is utilized.

Combined with the Dimethyl Benzyl Lauryl Ammonium Bromide in the disinfecting composition of the present invention is a diluter. The diluter of the present invention is a substantially pure, substantially de-ionized, and substantially bacteria free diluter, and preferably includes water which has been purified and de-ionized. Moreover, in the preferred embodiment the water is at least 98% pure, at least 98% de-ionized, and at least 98% bacteria free. Specifically, water at such a high purity and de-ionization level can be effectively combined with the Dimethyl Benzyl Lauryl Ammonium Bromide and will not cause a reaction with the Dimethyl Benzyl Lauryl Ammonium Bromide that could affect its strength or toxicity. For example, if residual minerals or other impurities are present in the water, when the pure Dimethyl Benzyl Lauryl Ammonium Bromide is initially combined with the water it will seek to interact with those minerals and may accordingly lose some of its potency, may lead to algae or tainting, or will not achieve a balanced state, before it is effectively diluted and provides the balanced base mixture. Indeed, once the balanced base mixture is attained the base mixture can then be exposed to some minerals and the like without loosing its balanced, safe and effective characteristics. It is understood that the pure, de-ionized, bacteria free water is preferably include in a quantity of at least 87% by volume, and preferably comprises the remaining quantity of the base mixture with the Dimethyl Benzyl Lauryl Ammonium Bromide. As such, in a preferred embodiment of the invention as used for topical skin disinfection close to 99% by volume of the base mixture is comprised by the pure, de-ionized, bacteria free water.

In the preferred embodiment, the water is provided at the high purity and de-ionization level through a precise and extensive treatment process. For example, an initial step preferably includes passing ordinary, preferably conventionally treated water through a clarification filter, such as a sand filter, so as to remove minerals and other impurities from the water. Next, the water is preferably passed through a carbon filter, which generally removes odor, taste, chlorine, magnesium, iron precipitates and other minerals and impurities from the water. The water is then softened, such as by passing through a water softener that eliminates calcium, magnesium and other smaller minerals and impurities. Preferably at this point, the water is subjected to treatment by reverse osmosis to further remove impurities and minerals. Indeed, it is noted that the treatment by reverse osmosis generally results in approximately 50% of the water being lost and 50% of the water continuing through the processing. Specifically, the remaining water is then preferably passed through a cationic resin filter and an anionic resin filter so as to effectively de-ionize the water. In the preferred embodiment, this process de-ionizes the water to a near 100% level, and indeed, after the previously described purification steps the water is already near 99% pure. However, in the preferred embodiment of the present invention additional steps are undertaken and a near 100% purity level is attained. For example, the water is also preferably passed through a polisher resin that further filters the water, and is subjected to UV radiation, such as from a UV light, in order to kill any (i.e. preferably at least 98%) germs or bacteria which may be present in the water. At that point, a further filter, such as a 1 micron filter is utilized to remove the "dead" bacteria and germs from the water such that it is 98% bacteria free. Lastly, in the preferred embodiment, the water is distilled, preferably by at least bi-distillation to achieve the substantially pure water. Of course, it is understood that the above recites the preferred method of treating the water used in the present invention, and that other methods may be developed or that the order or specific inclusion of the preceding steps may be modified. The pH of the pure water available for use in connection with the invention varies from one place to another. Therefore, depending on the pH of the water, there are two formulas, which provide alternate embodiments of the invention.

In some applications, such as the pharmaceutical and medical applications, but preferably in all applications, in addition to the Dimethyl Benzyl Lauryl Ammonium Bromide and pure, de-ionized, bacteria free water, the disinfecting composition of the present invention preferably includes a means to stabilize the mixture thereof and bring the base mixture to a pH level of between 6.8 and 7.2. The preferred method for doing so depends on the initial pH of the pure, deionized, bacteria-free water. Preferably, the means to stabilize the base mixture includes one or more stabilizers added to the base mixture of Dimethyl Benzyl Lauryl Ammonium Bromide and pure, de-ionized, bacteria free water. In particular, the disinfecting composition of the present invention in one preferred embodiment includes a first stabilizer which is structured to initially bring the pH level of the mixture to be between 6.8 and 7.2. Specifically, it is noted that in some circumstances, the pure, de-ionized, bacteria free water will typically have a pH level below 6.8. As a result, the first stabilizer is preferably an alkaline stabilizer, such as sodium hydroxide, which when added to the water elevates the pH level of the mixture to between 6.8 and 7.2. Moreover, although the precise quantity of the first stabilizer to be added to the base mixture will vary depending upon the amount of pH level modification to be achieved, typically less than 1% by volume of the disinfectant composition is desired.

It is also noted that in some circumstances, it may be desirable to boost or increase the strength of the disinfecting composition, and specifically the Dimethyl Benzyl Lauryl Ammonium Bromide, without increasing the concentration of Dimethyl Benzyl Lauryl Ammonium Bromide in the base mixture. In such a circumstance, and indeed in a preferred embodiment, the disinfecting composition of the preferred embodiment further includes a strengthening additive. Principally, the strengthening additive is structured to increase an overall strength and effectiveness of the disinfectant composition, and specifically the Dimethyl Benzyl Lauryl Ammonium Bromide. As a result, the Dimethyl Benzyl Lauryl Ammonium Bromide, although contained in substantially small, diluted quantities in order to substantially eliminate the harmful and/or toxic effects thereof, will still be substantially effective to kill germs, viruses, fuinguses and bacteria present on an article with which the disinfectant composition is utilized. This additional stabilizer, which in some circumstances may also take the place of the first stabilizer, is preferably added in a quantity of less than 2% of the total volume, with the actual amount depending upon the initial pH level. Moreover, in the preferred embodiment, this additional stabilizer includes ammonium sulfate.

If as previously recited, the preferred pH level of between 6.8 and 7.2 is to be attained, and the strengthening additive is utilized and the pH level has accordingly been elevated, the present invention further includes a third stabilizer. The third stabilizer is preferably provided in a quantity of less than 1% by volume, with the actual amount again depending upon the pH levels, and is structured to be included with the disinfecting composition after the first and second stabilizers have been added and have taken effect. The third stabilizer is preferably acidic, such as citric acid, and is structured to lower the pH level of the disinfectant composition back to the pH level of between 6.8 and 7.2. Such lowering to the pH level of between 6.8 and 7.2 thereby produces a substantially stable and balanced disinfecting composition which has proven to be highly powerful and effective, but which maintains the non-toxic, non-corrosive, colorless and generally non-harmful qualities.

Moreover, the disinfecting composition of the present invention can then be effectively combined with a variety of other compositions, such as cleaners, soaps, colorizing agents and the like, depending upon the particular use of the product. For example, it is contemplated that the disinfecting composition may be utilized as part of a gel or cream type solution which can be applied topically to living human or animal patients, if necessary. With regard to these additives or carriers, it is preferred that products containing ingredients which adversely effect the strength or toxicity of the Dimethyl Benzyl Lauryl Ammonium Bromide be avoided. For example, some such ingredients include basic acids, bleach, zinc sulfate, nitric acid, chlorine, fluorine, iodine, and chlorophyll, with other adversely reacting ingredients existing and or to be determined through normal experimentation. Furthermore, it is noted that the disinfecting composition of the present invention, unlike other compositions may have a substantially unlimited shelf life if maintained at normal temperatures, such as between −5 degrees C. and 130 degrees C.

The present invention is also directed towards a method of manufacturing a disinfecting composition which is highly safe and effective. In particular, the method of the present invention includes an initial phase of de-ionizing and purifying a quantity of water. More particularly, by preferably utilizing the previously described, preferred method of purification and de-ionization, the water is treated so as to attain purity levels preferably in excess of 98%, and de-ionization levels preferably in excess of 98%. Such treatment of the water accordingly substantially eliminates mineral deposits, bacteria, algae, potentially reactive ions and other contaminants from the water such that they will not interact with and in turn adversely effect the subsequent ingredient.

Specifically, a quantity of the water is measured and is mixed with a corresponding quantity of Dimethyl Benzyl Lauryl Ammonium Bromide. More particularly, this base mixture preferably includes a measurement of less than 9.4%, but preferably between about 0.05% and 9% by volume of preferably over 91% pure Dimethyl Benzyl Lauryl Ammonium Bromide combined with the water.

Once the base mixture of Dimethyl Benzyl Lauryl Ammonium Bromide and pure, de-ionized, bacteria free water has been made, in a preferred embodiment, a pH level of the base mixture is preferably tested and identified. Although it may be possible to skip this test, the next step of the preferred embodiment includes the addition of a first stabilizer to the mixture in order to bring a pH level of the mixture to between approximately 6.8 and 7.2. Of course, the ideal pH level would be 7 in this case. Moreover, the preferred stabilizer includes an alkaline stabilizer, such as sodium hydroxide, measured to a quantity of less than 1% per volume and added to the mixture. Of course, the specific quantity of the first stabilizer to be added will ultimately depend upon the pH level of the mixture prior to its addition, as varying pH levels will often be exhibited, depending upon the specific properties of the water being utilized with the Dimethyl Benzyl Lauryl Ammonium Bromide. Typically, however, pH levels below 6.8 will be exhibited by the initial mixture of Dimethyl Benzyl Lauryl Ammonium Bromide and demineralized, de-ionized water.

At this point, a pH of the mixture can again be measured to ensure that the pH level of the mixture is generally between 6.8 and 7.2, and the preferred embodiment includes an additional step of adding a strengthening agent, preferably in the form of a second stabilizer, to the mixture. The second stabilizer is preferably ammonium sulfate and is structured to elevate the overall pH of the mixture to a point above 7.2, and preferably to a pH level of between about 7.8 and 8.2. In this regard, less than 2% per volume of the ammonium sulfate is preferably added to the mixture, the specific amounts depending upon the overall quantity of the mixture and the pH level before addition of the ammonium sulfate. It is also noted, however, that if desired, the initial step of bringing the pH level to between 6.8 and 7.2 can be skipped, and the second stabilizer can be immediately added. In such a case, however, excess quantities of the specific second stabilizer may ultimately be required.

Lastly in this preferred embodiment, a third stabilizer is added to the mixture. In this regard, preferably less than 1% per volume of an acidic stabilizer is added to the mixture in order to bring the overall pH level of the mixture back down to between 6.8 and 7.2, and preferably to 7. In the preferred embodiment citric acid is utilized as the acidic stabilizer due to its generally neutral properties outside of its pH level variant effects. Accordingly, the finished disinfectant composition will be stabilized at a level of between 6.8 and 7.2 and contains Dimethyl Benzyl Lauryl Ammonium Bromide in sufficient quantities and in a sufficient strength to be substantially effective to disinfect without being toxic, colored, corrosive, flammable or vapor producing. This disinfecting composition, can then be added to a variety of other neutral compositions which may make the product more suitable for its use.

By way of example, an ideal mixture of the disinfectant composition of the present invention which is suitable for a topical skin disinfectant use will preferably include 0.24% by volume of Dimethyl Benzyl Lauryl Ammonium Bromide mixed with +99% pure, +99% de-ionized, +99% bacteria free water to define the base mixture. Since the added strength and pH level balance is preferred, in the present embodiment 0.24% by volume of sodium hydroxide was added to the base mixture thereby elevating the pH of the overall mixture to the desired levels. At that point, 0.58% by volume of ammonium sulfate was added to the overall mixture to add strength, and in turn a pH level of the mixture was seen to increase. Lastly, 0.33% by volume of citric acid was added to the mixture, once again returning the overall pH level of the mixture to within the acceptable range.

Similarly, in a second example, which is preferably for use operating room disinfectant purposes, 3.22% by volume of the Dimethyl Benzyl Lauryl Ammonium Bromide is combined with the pure, de-ionized, bacteria free water, whereafter 0.21% by volume of sodium hydroxide, followed by 0.63% by volume of ammonium sulfate and 0.38% by volume of citric acid are added.

By way of summary, it is again noted that the pH of the pure water to be used in the formula of the invention varies from one place to another. Therefore, depending on the pH of the water, there are two alternate embodiments. Each reflects a different formula in which the components are mixed in the order cited below:

First Alternative (Water High pH)
a. Pure water, substantially bacteria and ion free, with pH between about 7.0 and 8.8.
b. Dimethyl benzyl lauryl ammonium bromide is added in the amount of 0.05 to 9.4 g. per 100 ml. of solution, and preferably 0.17 g. per 100 ml. of solution. Once the dimethyl benzyl lauryl ammonium bromide is added, the pH increases to about 8.8 to 9.2.
c. Ammonium sulfate, preferably in a solution of approximately 50 g. per 100 ml. water (preferably the substantially pure, substantially de-ionized, substantially bacteria free water otherwise used in this invention) is added, until the pH decreases to about 7.7 to 7.8. The ammonium sulfate is added to increase the strength and effectiveness of the bromide compound. If desired, citric acid may then be added as a stabilizer until the pH of the formula decreases to between about 6.8 and 7.2 (although additional ammonium sulfate solution may be added to achieve substantially the same pH adjustment).

Second Alternative (Water Low pH)
a. Pure water, substantially bacteria and ion free, with pH between about 5.0. and 6.8.
b. Sodium hydroxide is added as the first stabilizer until the pH of the pure water rises to 7.2.
c. Dimethyl benzyl lauryl ammonium bromide is added in the amount of 0.05 to 9.4 g. per 100 ml. of solution, and preferably 0.17 g. per 100 ml. of solution. Once the dimethyl benzyl lauryl ammonium bromide is added, the pH increases to about 8.8. to 9.2.
d. Ammonium sulfate, preferably in a solution of approximately 50 g. per 100 ml. water (preferably the substantially pure, substantially de-ionized, substantially bacteria free water otherwise used in this invention) is added, until the pH decreases to about 7.7 to 7.8.
e. If desired, citric acid may be added as a second stabilizer until the pH of the formula decrease to between 6.8. and 7.2 (although additional ammonium sulfate solution may be added to achieve substantially the same pH adjustment).

In these two formulas, there are various additives, some of which are stabilizers. In the first alternative, only citric acid (if used) acts as a stabilizer. In the second, both sodium hydroxide and the citric acid (if used) act as stabilizers. Finally, it should be mentioned that other components could be added to the formula in order to give it a specific odor or color.

These compositions may be effectively used as a virusides, germicides, sporicides, bactericides, fungicides, cold sterilizers and food preservatives.

It is understood that the disinfecting composition of the present invention has a variety of further uses which are contemplated, and which are yet to be determined and/or discovered. Indeed, it is a specific quality of the disinfectant solution of the present invention as a highly effective disinfectant, bactericide, cold sterilizer, fungicide, virucide that is also non-toxic, non-corrosive, colorless, non-flammable, non-staining, stable at normal temperatures, such as between −5 degrees C. and 130 degrees C., and produces no vapors or other harmful side effects which expands the possibility of ultimate end uses of the disinfecting composition of the present invention. The preferred uses of the present invention, however, are as a cold sterilizer for surgical instruments, as a topical disinfectant for any surface or for a living subject, and for the disinfecting of food, such as produce and various plants, with the actual concentrations of the primary ingredients varying, preferably within the specified ranges, depending upon the uses.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described.

What is claimed is:

1. A disinfectant composition comprising:
a) dimethyl benzyl lauryl ammonium bromide;
b) water, said water being at least about 98% pure, at least about 98% de-ionized, and at least about 98% bacteria-free;
c) a first additive, if necessary, to adjust the pH level of said composition to between about 6.8 and 7.2;
d) a second additive comprising ammonium sulfate;
e) a third additive, if necessary, said third additive being acidic, to adjust the pH level of said composition to between about 6.8 and 7.2.

2. The disinfectant composition as recited in claim 1 wherein said third additive comprises citric acid.

3. A disinfectant composition comprising:
  a) a base mixture, said base mixture comprising:
    between 0.05% and 9% by volume of dimethyl benzyl lauryl ammonium bromide, and
    at least about 98% pure, at least about 98% de-ionized, at least about 98% bacteria free water;
  b) a first additive structured to adjust if necessary the pH level of the disinfectant composition between about 6.8 and 7.2, said first additive added to said mixture prior to the addition of said dimethyl benzyl lauryl ammonium bromide;
  c) ammonium sulfate added as a second additive after said first additive and structured to increase the effectiveness of said dimethyl benzyl lauryl ammonium bromide;
  d) a third additive added after said first additive and said ammonium sulfate as said second additive, and structured to lower said pH level of the disinfectant composition to between about 6.8 and 7.2.

4. The disinfectant composition as recited in claim 3 including less than 2% by volume of said ammonium sulfate.

* * * * *